United States Patent

Sipinski

(10) Patent No.: US 8,668,115 B2
(45) Date of Patent: *Mar. 11, 2014

(54) FUNCTIONAL OPERATION AND TIMING CONTROL IMPROVEMENTS FOR DISPENSERS

(71) Applicant: Gene Sipinski, Elgin, IL (US)

(72) Inventor: Gene Sipinski, Elgin, IL (US)

(73) Assignee: S.C. Johnson & Son, Inc., Racine, WI (US)

(*) Notice: Subject to any disclaimer, the term of this patent is extended or adjusted under 35 U.S.C. 154(b) by 0 days.

This patent is subject to a terminal disclaimer.

(21) Appl. No.: 13/890,632

(22) Filed: May 9, 2013

(65) Prior Publication Data

US 2013/0240560 A1    Sep. 19, 2013

Related U.S. Application Data

(63) Continuation of application No. 12/605,907, filed on Oct. 26, 2009, now Pat. No. 8,459,499.

(51) Int. Cl.
*B67B 7/00* (2006.01)

(52) U.S. Cl.
USPC .......... 222/1; 222/23; 222/63; 222/504; 222/646; 222/649; 239/70; 239/99; 4/228.1; 422/5

(58) Field of Classification Search
USPC ............ 422/5; 239/69–70, 99; 4/228.1, 623; 222/1, 23, 36, 52, 63, 183, 333, 504, 222/638, 644–649, 402.1, 325
See application file for complete search history.

(56) References Cited

U.S. PATENT DOCUMENTS

| D103,209 S | 2/1937 | Beiser |
| D128,935 S | 8/1941 | Derham et al. |
| 2,560,817 A | 7/1951 | Pfeifer |
| D180,916 S | 9/1957 | Perlman |
| 2,928,573 A | 3/1960 | Edelstein |
| 3,165,238 A | 1/1965 | Wiley |

(Continued)

FOREIGN PATENT DOCUMENTS

| AU | 4932300 | 11/2000 |
| AU | 752399 | 9/2002 |

(Continued)

OTHER PUBLICATIONS

Web Page "Air Wick FreshMatic" @ http://www.gnpd.com/sinatra/gnpd&lang=uk/images/zoom&id=342358&pic_num=0&xOff . . . dated Mar. 7, 2005 (1 page).

(Continued)

*Primary Examiner* — Paul R Durand
*Assistant Examiner* — Andrew P Bainbridge

(57) ABSTRACT

A method of operating a dispensing unit includes the steps of applying a power source to a dispensing unit that includes a container and performing a startup procedure in response to applying the power source. The startup procedure also includes the step of performing an activation sequence that discharges a fluid from the container. The method further includes the step of performing an active mode procedure after the startup procedure without providing a lockout period in between. The active mode procedure includes activating a sensor associated with the dispensing unit, performing an activation sequence that discharges the fluid from the container when the sensor detects sensory input, and performing a transition procedure.

20 Claims, 3 Drawing Sheets

(56) References Cited

U.S. PATENT DOCUMENTS

| | | |
|---|---|---|
| 3,228,609 A | 1/1966 | Edelstein et al. |
| 3,289,886 A | 12/1966 | Goldsholl et al. |
| 3,368,717 A | 2/1968 | Weber III |
| 3,584,766 A | 6/1971 | Hart |
| 3,589,563 A | 6/1971 | Carragan et al. |
| 3,615,041 A | 10/1971 | Bischoff |
| 3,643,836 A | 2/1972 | Hunt |
| 3,732,509 A | 5/1973 | Florant et al. |
| 3,739,944 A | 6/1973 | Rogerson |
| 3,952,916 A | 4/1976 | Phillips |
| 3,974,941 A | 8/1976 | Mettler |
| D243,017 S | 1/1977 | Fossella |
| 4,006,844 A | 2/1977 | Corris |
| 4,063,664 A | 12/1977 | Meetze, Jr. |
| 4,235,373 A | 11/1980 | Clark |
| 4,483,466 A | 11/1984 | Gutierrez |
| 4,544,086 A | 10/1985 | Hill et al. |
| 4,690,312 A | 9/1987 | Crapser et al. |
| 4,816,951 A | 3/1989 | Zago |
| 4,830,791 A | 5/1989 | Muderlak et al. |
| 4,877,989 A | 10/1989 | Drews et al. |
| 4,967,935 A | 11/1990 | Celest |
| 4,989,755 A | 2/1991 | Shiau |
| 5,014,881 A | 5/1991 | Andris |
| 5,014,884 A | 5/1991 | Wunsch |
| 5,038,972 A | 8/1991 | Muderlak et al. |
| 5,055,822 A | 10/1991 | Campbell et al. |
| 5,069,876 A | 12/1991 | Oshinsky |
| 5,134,961 A | 8/1992 | Giles et al. |
| 5,198,157 A | 3/1993 | Bechet |
| 5,249,718 A | 10/1993 | Muderiak |
| 5,269,445 A | 12/1993 | Tobler |
| 5,337,926 A | 8/1994 | Drobish et al. |
| 5,342,584 A | 8/1994 | Fritz et al. |
| 5,353,744 A | 10/1994 | Custer |
| 5,383,580 A | 1/1995 | Winder |
| RE34,847 E | 2/1995 | Muderlak et al. |
| 5,392,768 A | 2/1995 | Johansson et al. |
| 5,394,866 A | 3/1995 | Ritson et al. |
| 5,445,324 A | 8/1995 | Berry et al. |
| 5,449,117 A | 9/1995 | Muderlak et al. |
| 5,450,336 A | 9/1995 | Rubsamen et al. |
| 5,489,047 A | 2/1996 | Winder |
| 5,497,764 A | 3/1996 | Ritson et al. |
| 5,503,303 A | 4/1996 | LaWare et al. |
| 5,520,166 A | 5/1996 | Ritson et al. |
| 5,522,378 A | 6/1996 | Ritson et al. |
| 5,531,344 A | 7/1996 | Winner |
| 5,542,605 A | 8/1996 | Campau |
| 5,591,409 A | 1/1997 | Watkins |
| 5,622,162 A | 4/1997 | Johansson et al. |
| D380,821 S | 7/1997 | Chen |
| 5,647,388 A | 7/1997 | Butler, Jr. et al. |
| 5,657,910 A | 8/1997 | Keyser |
| 5,673,825 A | 10/1997 | Chen |
| 5,676,283 A | 10/1997 | Wang |
| 5,695,091 A | 12/1997 | Winings et al. |
| 5,702,036 A | 12/1997 | Ferrara, Jr. |
| 5,735,918 A | 4/1998 | Barradas |
| 5,743,251 A | 4/1998 | Howell et al. |
| 5,743,252 A | 4/1998 | Rubsamen et al. |
| 5,755,218 A | 5/1998 | Johansson et al. |
| 5,772,074 A | 6/1998 | Dial et al. |
| 5,810,265 A | 9/1998 | Cornelius et al. |
| 5,823,390 A | 10/1998 | Muderlak et al. |
| 5,826,570 A | 10/1998 | Goodman et al. |
| 5,853,129 A | 12/1998 | Spitz |
| 5,884,808 A | 3/1999 | Muderlak |
| 5,908,140 A | 6/1999 | Muderlak |
| 5,922,247 A | 7/1999 | Shoham et al. |
| 5,924,597 A | 7/1999 | Lynn |
| 5,938,076 A | 8/1999 | Ganzeboom |
| 6,000,658 A | 12/1999 | McCall, Jr. |
| 6,006,957 A | 12/1999 | Kunesh |
| 6,026,987 A | 2/2000 | Burnett et al. |
| 6,029,659 A | 2/2000 | O'Connor |
| 6,036,108 A | 3/2000 | Chen |
| 6,039,212 A | 3/2000 | Singh |
| 6,092,912 A | 7/2000 | Nelson |
| 6,182,904 B1 | 2/2001 | Ulczynski et al. |
| 6,216,925 B1 | 4/2001 | Garon |
| 6,237,812 B1 | 5/2001 | Fukada |
| 6,254,065 B1 | 7/2001 | Ehrensperger et al. |
| 6,267,297 B1 | 7/2001 | Contadini et al. |
| 6,293,442 B1 | 9/2001 | Mollayan |
| 6,297,297 B1 | 10/2001 | Brookman et al. |
| 6,394,310 B1 | 5/2002 | Muderlak et al. |
| 6,409,093 B2 | 6/2002 | Ulczynski et al. |
| D460,544 S | 7/2002 | Garcia |
| 6,419,122 B1 | 7/2002 | Chown |
| 6,478,199 B1 | 11/2002 | Shanklin et al. |
| 6,510,561 B1 | 1/2003 | Hammond et al. |
| 6,516,796 B1 | 2/2003 | Cox et al. |
| 6,517,009 B2 | 2/2003 | Yahav |
| 6,533,141 B1 | 3/2003 | Petterson et al. |
| 6,540,155 B1 | 4/2003 | Yahav |
| 6,554,203 B2 | 4/2003 | Hess et al. |
| 6,567,613 B2 | 5/2003 | Rymer |
| D476,070 S | 6/2003 | Millan |
| 6,581,915 B2 | 6/2003 | Bartsch et al. |
| 6,588,627 B2 | 7/2003 | Petterson et al. |
| D478,003 S | 8/2003 | Bodker et al. |
| 6,612,464 B2 | 9/2003 | Petterson et al. |
| 6,644,507 B2 | 11/2003 | Borut et al. |
| D484,585 S | 12/2003 | Upson |
| 6,669,105 B2 | 12/2003 | Bryan et al. |
| 6,688,492 B2 | 2/2004 | Jaworski et al. |
| 6,694,536 B1 | 2/2004 | Haygreen |
| 6,713,024 B1 | 3/2004 | Arnell et al. |
| D488,548 S | 4/2004 | Lablaine |
| 6,722,529 B2 | 4/2004 | Ceppaluni et al. |
| 6,739,479 B2 | 5/2004 | Contadini et al. |
| D491,798 S | 6/2004 | Buthier |
| 6,769,580 B2 | 8/2004 | Muderlak et al. |
| 6,785,911 B1 | 9/2004 | Percher |
| 6,790,408 B2 | 9/2004 | Whitby et al. |
| 6,830,164 B2 | 12/2004 | Michaels et al. |
| 6,832,701 B2 | 12/2004 | Schiller |
| 6,837,396 B2 | 1/2005 | Jaworski et al. |
| 6,877,636 B2 | 4/2005 | Speckhart et al. |
| 6,926,211 B2 | 8/2005 | Bryan et al. |
| 6,971,560 B1 | 12/2005 | Healy et al. |
| 6,974,091 B2 | 12/2005 | McLisky |
| 6,978,947 B2 | 12/2005 | Jin |
| 7,182,227 B2 | 2/2007 | Poile et al. |
| 7,195,139 B2 | 3/2007 | Jaworski et al. |
| 7,222,760 B1 | 5/2007 | Tsay |
| 7,223,361 B2 | 5/2007 | Kvietok et al. |
| 8,459,499 B2 * | 6/2013 | Sipinski .......................... 222/1 |
| 2002/0020756 A1 | 2/2002 | Yahav |
| 2002/0074349 A1 | 6/2002 | Michaels et al. |
| 2002/0130146 A1 | 9/2002 | Borut et al. |
| 2002/0146243 A1 | 10/2002 | Rymer |
| 2002/0166871 A1 | 11/2002 | Muderlak et al. |
| 2003/0000524 A1 | 1/2003 | Anderson et al. |
| 2003/0079744 A1 | 5/2003 | Bonney et al. |
| 2003/0132254 A1 | 7/2003 | Giangreco |
| 2004/0011885 A1 | 1/2004 | McLisky |
| 2004/0028551 A1 | 2/2004 | Kvietok et al. |
| 2004/0033171 A1 | 2/2004 | Kvietok et al. |
| 2004/0074935 A1 | 4/2004 | Chon |
| 2004/0155056 A1 | 8/2004 | Yahav |
| 2004/0219863 A1 | 11/2004 | Willacy |
| 2005/0004714 A1 | 1/2005 | Chen |
| 2005/0023287 A1 | 2/2005 | Speckhart et al. |
| 2005/0067439 A1 | 3/2005 | Furner et al. |
| 2005/0139624 A1 | 6/2005 | Hooks et al. |
| 2005/0201944 A1 | 9/2005 | Kvietok et al. |
| 2005/0224596 A1 | 10/2005 | Panopoulos |
| 2006/0011737 A1 | 1/2006 | Amenos et al. |
| 2006/0037532 A1 | 2/2006 | Eidson |
| 2006/0060615 A1 | 3/2006 | McLisky |
| 2006/0067859 A1 | 3/2006 | Laudamiel-Pellet et al. |
| 2006/0076366 A1 | 4/2006 | Furner et al. |

(56) References Cited

U.S. PATENT DOCUMENTS

| | | |
|---|---|---|
| 2006/0083632 A1 | 4/2006 | Hammond et al. |
| 2006/0151546 A1 | 7/2006 | McLisky |
| 2006/0153733 A1 | 7/2006 | Sassoon |
| 2006/0175341 A1 | 8/2006 | Rodrian |
| 2006/0175357 A1 | 8/2006 | Hammond |
| 2006/0175426 A1 | 8/2006 | Schramm et al. |
| 2006/0191955 A1 | 8/2006 | McLisky |
| 2006/0196576 A1 | 9/2006 | Fleming et al. |
| 2006/0219740 A1 | 10/2006 | Bayer |
| 2006/0229232 A1 | 10/2006 | Contadini et al. |
| 2006/0243762 A1 | 11/2006 | Sassoon |
| 2007/0012718 A1 | 1/2007 | Schramm et al. |
| 2007/0036673 A1 | 2/2007 | Selander |
| 2007/0138326 A1 | 6/2007 | Hu |
| 2007/0158359 A1 | 7/2007 | Rodrian |
| 2007/0199952 A1 | 8/2007 | Carpenter et al. |
| 2007/0217945 A1 | 9/2007 | Selander |
| 2008/0056691 A1 | 3/2008 | Wingo et al. |
| 2008/0156896 A1 | 7/2008 | Anderson et al. |
| 2009/0127351 A1 | 5/2009 | Powell et al. |

FOREIGN PATENT DOCUMENTS

| | | |
|---|---|---|
| DE | 19803696 | 8/1999 |
| DE | 10392689 | 4/2005 |
| DE | 10392794 | 6/2005 |
| EP | 038598 | 10/1981 |
| EP | 401060 | 12/1990 |
| EP | 676133 | 10/1995 |
| EP | 1184083 | 3/2002 |
| EP | 1214949 | 6/2002 |
| EP | 1316514 | 6/2003 |
| EP | 1382399 | 1/2004 |
| EP | 1407790 | 4/2004 |
| EP | 1430958 | 6/2004 |
| EP | 1522506 | 4/2005 |
| EP | 1695720 | 8/2006 |
| EP | 1726315 | 11/2006 |
| FR | 2671294 | 7/1992 |
| GB | 2094407 | 9/1982 |
| GB | 2248888 | 4/1992 |
| GB | 2305261 | 4/1997 |
| GB | 2375710 | 11/2002 |
| JP | 2002113398 | 4/2002 |
| WO | 8805758 | 8/1988 |
| WO | 9115409 | 10/1991 |
| WO | 9519304 | 7/1995 |
| WO | 9529106 | 11/1995 |
| WO | 9934266 | 7/1999 |
| WO | 0047335 | 8/2000 |
| WO | 0064498 | 11/2000 |
| WO | 0064802 | 11/2000 |
| WO | 0075046 | 12/2000 |
| WO | 0078467 | 12/2000 |
| WO | 0107703 | 2/2001 |
| WO | 0121226 | 3/2001 |
| WO | 0126448 | 4/2001 |
| WO | 0166157 | 9/2001 |
| WO | 0240177 | 5/2002 |
| WO | 0240376 | 5/2002 |
| WO | 02072161 | 9/2002 |
| WO | 02079679 | 10/2002 |
| WO | 02087976 | 11/2002 |
| WO | 02094014 | 11/2002 |
| WO | 03005873 | 1/2003 |
| WO | 03037748 | 5/2003 |
| WO | 03037750 | 5/2003 |
| WO | 03042068 | 5/2003 |
| WO | 03062094 | 7/2003 |
| WO | 03062095 | 7/2003 |
| WO | 03068412 | 8/2003 |
| WO | 03068413 | 8/2003 |
| WO | 03086902 | 10/2003 |
| WO | 03086947 | 10/2003 |
| WO | 03099682 | 12/2003 |
| WO | 03104109 | 12/2003 |
| WO | 2004002542 | 1/2004 |
| WO | 2004043502 | 5/2004 |
| WO | 2004067963 | 8/2004 |
| WO | 2004073875 | 9/2004 |
| WO | 2004081303 | 9/2004 |
| WO | 2004093927 | 11/2004 |
| WO | 2004093928 | 11/2004 |
| WO | 2004105816 | 12/2004 |
| WO | 2004105817 | 12/2004 |
| WO | 2004105818 | 12/2004 |
| WO | 2004110507 | 12/2004 |
| WO | 2005001212 | 1/2005 |
| WO | 2005014060 | 2/2005 |
| WO | 2005018691 | 3/2005 |
| WO | 2005023679 | 3/2005 |
| WO | 2005072059 | 8/2005 |
| WO | 2005072522 | 8/2005 |
| WO | 2006012248 | 2/2006 |
| WO | 2006044416 | 4/2006 |
| WO | 2006058433 | 6/2006 |
| WO | 2006064187 | 6/2006 |
| WO | 2006084317 | 8/2006 |
| WO | 2006104993 | 10/2006 |
| WO | 2006105652 | 10/2006 |
| WO | 2006108043 | 10/2006 |
| WO | 2007029044 | 3/2007 |
| WO | 2007045828 | 4/2007 |
| WO | 2007052016 | 5/2007 |
| WO | 2007064188 | 6/2007 |
| WO | 2007064189 | 6/2007 |
| WO | 2007064199 | 6/2007 |

OTHER PUBLICATIONS

Web Page "Air Wick FreshMatic" @ http://www.cleanware.co.nz/product_info.php?products_id=159 dated Mar. 7, 2005 (1 page).
Web Page http://www.cleanware.co.nz/images/client/AirWick2.jpg dated Mar. 7, 2005 (1 page).
Web Page "FreshMatic Refill Citrus" @ http://www.cleanware.co.nz/product_info.php?products_id=161 dated Mar. 7, 2005 (1 page).
Web Page "Air Wick Frequently Asked Questions" @ http://www.airwick.co.uk/faqs_page/faqs.html dated Mar. 7, 2005 (6 pages).
Web Page "Air Wick Personalize Your Atmosphere with the Fragrances You Love" @ http://www.airwick.co.uk/product_page/product.html dated Mar. 7, 2005 (5 pages).
Extended European Search Report for EP Application No. 07011131.5-2425 (based on PCT/US2005/036576) dated Aug. 27, 2007.
Extended European Search Report for EP Application No. 07011132.3-2425 (based on PCT/US2005/036576) dated Aug. 27, 2007.
PCT/US2008/003317 International Search Report and Written Opinion dated Nov. 6, 2008.
Office Action in U.S. Appl. No. 11/247,793 dated Aug. 12, 2009.
Response A dated Sep. 18, 2009.
Office Action in U.S. Appl. No. 11/247,793 dated Jan. 20, 2010.
Amendment A dated Mar. 11, 2010.
Office Action in U.S. Appl. No. 11/247,793 dated Mar. 15, 2010.
PCT/US2010/002835 International Search Report dated Feb. 2, 2011.

* cited by examiner

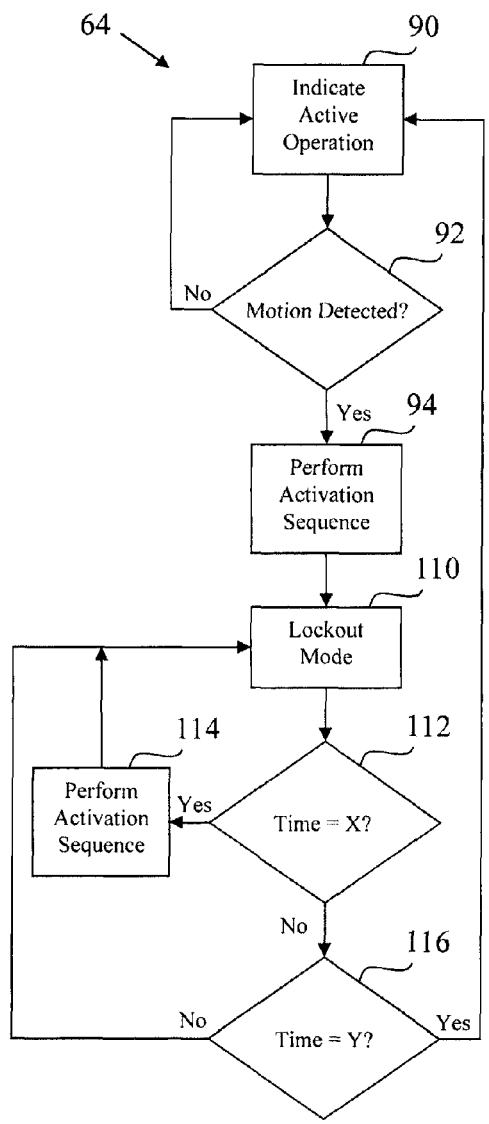
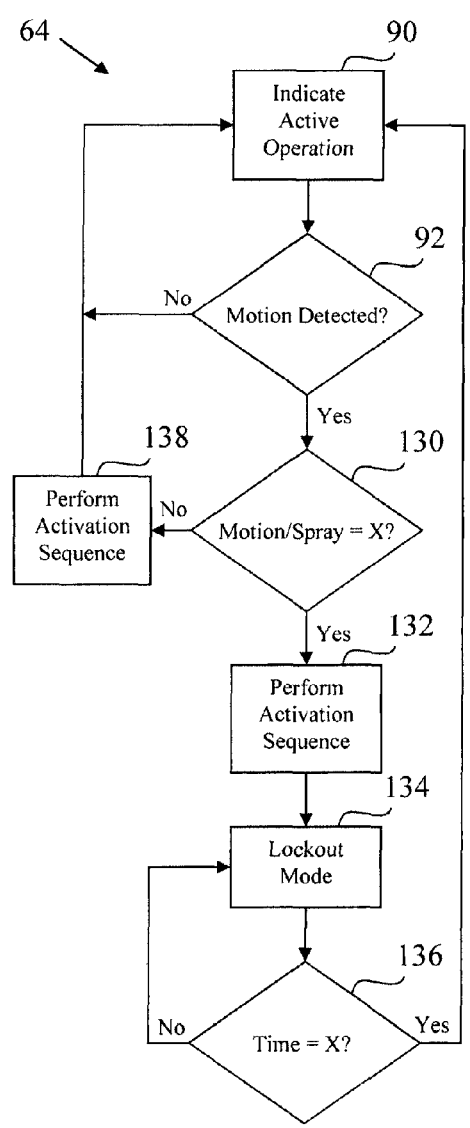
FIG. 7                    FIG. 8

FUNCTIONAL OPERATION AND TIMING CONTROL IMPROVEMENTS FOR DISPENSERS

CROSS REFERENCE TO RELATED APPLICATIONS

This application is a continuation of U.S. application Ser. No. 12/605,907, filed Oct. 26, 2009, entitled "Dispensers and Functional Operation and Timing Control Improvements for Dispensers."

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Invention

The present disclosure relates to dispensers for discharging volatile materials from a container and methods for operating same.

2. Description of the Background of the Invention

Diffusion devices or dispensers are used to dispense volatile materials, such as perfumes, deodorizers, insecticides, insect repellants, and the like. Many such devices are passive diffusion devices that require only ambient air flow to dispense the volatile material, while other devices are active diffusion devices. Active diffusion devices are found in a variety of forms, some include fans and/or heaters to aid in the dispersal of volatile materials, others actuate a valve stem of an aerosol container to dispense a volatile material contained therein, still others utilize an ultrasonic transducer to break up a liquid volatile material into droplets that are ejected from the device, and yet others include any combination of the above or any other known type of active diffusion device. Various examples of such devices can be found in Helf et al. U.S. patent application Ser. No. 11/401,572, Beland et al. U.S. patent application Ser. No. 11/801,554, Helf et al. U.S. patent application Ser. No. 11/893,456, Helf et al. U.S. patent application Ser. No. 11/893,476, Helf et al. U.S. patent application Ser. No. 11/893,489, Helf et al. U.S. patent application Ser. No. 11/893,532, Sipinski et al. U.S. patent application Ser. No. 12/080,336, Sipinski et al. U.S. patent application Ser. No. 12/157,705, Pedrotti et al. U.S. Pat. No. 6,917,754, and Schwarz U.S. Pat. No. 7,540,473, all of which are incorporated herein by reference in their entireties. Further, some active diffusion devices include a sensor to detect motion or light in a space, wherein such devices dispense a volatile material in response to signals from the sensor.

Early diffusion devices that included sensors were developed to operate according to predefined operating methodologies for use in such places as restrooms to dispense perfumes or deodorizers to combat malodors. However, when a need arose for diffusion devices to be used in other environments, e.g., a living room, an office space, a factory floor, an outdoor area, etc., prior art devices that were developed for use in restrooms were found to lack the versatility necessary to be utilized in new environments. Consequently, a need has arisen for dispensers to provide an improved user experience and to enable a user to control the diffusion of a fragrance in different environments. The present disclosure relates to solutions to address such needs.

SUMMARY OF THE INVENTION

According to one embodiment, a method of operating a dispensing unit includes the steps of applying a power source to a dispensing unit that includes a container and performing a startup procedure in response to applying the power source. The startup procedure includes performing an activation sequence that discharges a fluid from the container. The method further includes the step of performing an active mode procedure after the startup procedure without providing a lockout period therebetween. The active mode procedure includes activating a sensor associated with the dispensing unit, performing an activation sequence that discharges the fluid from the container when the sensor detects sensory input, and performing a transition procedure.

According to another embodiment, a method of operating a dispensing unit includes the steps of applying a power source to a dispensing unit that includes a container and performing a startup procedure in response to applying the power source. The startup procedure includes performing an activation sequence that discharges a fluid from the container. The method further includes the step of performing an active mode procedure after the startup procedure without providing a lockout period therebetween. The active mode procedure includes detecting sensory input by a sensor associated with the dispensing unit and performing a transition procedure.

According to a further embodiment, a method of operating a dispensing unit includes the steps of applying a power source to a dispensing unit that includes a container and performing a startup procedure in response to applying the power source. The startup procedure includes providing a sleep period and performing an activation sequence that discharges a fluid from the container immediately after the sleep period has elapsed. The method further includes the step of performing an active mode procedure after the startup procedure. The active mode procedure includes activating a sensor associated with the dispensing unit, performing an activation sequence that discharges the fluid from the container when the sensor detects sensory input, and performing a transition procedure. The transition procedure includes providing a timeout period during which one or more automatic activation sequences are performed independent of any sensory input and a subsequent active mode procedure is initiated after the expiration of the timeout period.

Other aspects and advantages of the present invention will become apparent upon consideration of the following detailed description.

BRIEF DESCRIPTION OF THE DRAWINGS

FIG. 7 is a flowchart that illustrates a further embodiment of the active mode procedure of FIG. 5; and FIG. 8 is a flowchart that illustrates yet another embodiment of the active mode procedure of FIG. 5.

DETAILED DESCRIPTION OF THE DRAWINGS

Figure 1:
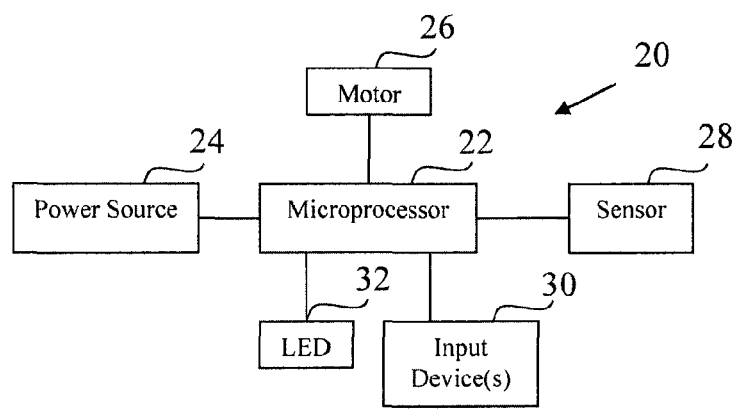
FIG. 1 is a block diagram of one embodiment of a dispenser.

FIG. 1 illustrates a device 20 that includes a microprocessor 22, a power source 24, a motor 26, a sensor 28, one or more input devices 30 such as switches, dials, keypads, pushbuttons, etc., and a light source 32, e.g., a light emitting diode ("LED"). The power source 24 supplies power to the microprocessor 22 and to the other components, wherein the microprocessor 22 is further coupled to the other components and executes programming to control the operation thereof. In one embodiment, the microprocessor 22 may be an ATtinyl 3V based microcontroller, such as those manufactured by Atmel Corporation, of 2325 Orchard Parkway, San Jose, Calif. 95131. However, it is contemplated that any type of microcontroller known to those of skill in the art may be used with the present embodiments.

Figure 2:
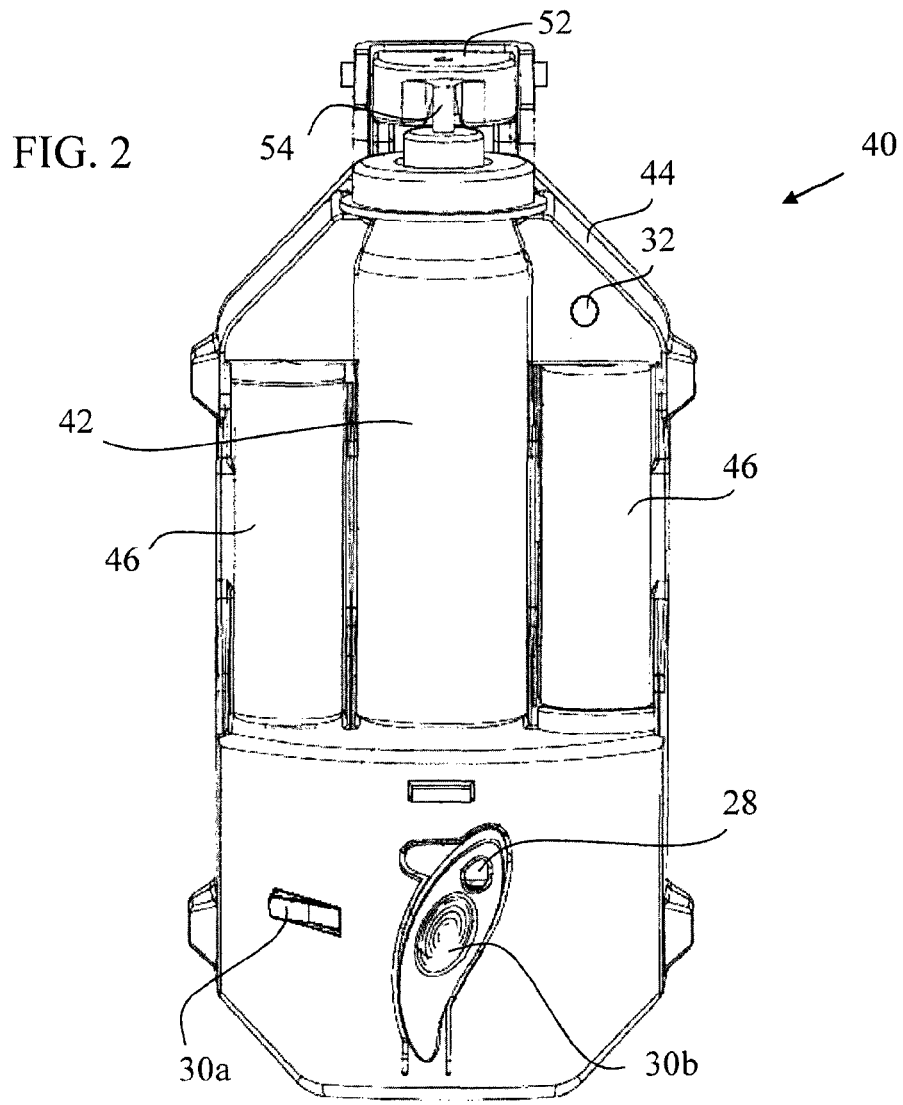
FIG. 2 is an isometric view of a dispenser according to another embodiment.

FIG. 2 illustrates an embodiment of the device 20 of FIG. 1 implemented as a dispenser 40 for dispensing the contents of an aerosol container 42. The dispenser 40 may be one of the devices described in Carpenter et al. U.S. patent application Ser. No. 11/725,402, which is incorporated herein by reference in its entirety. The dispenser 40 includes a housing 44 that is adapted to receive the aerosol container 42 and batteries 46. In addition, the dispenser 40 includes a selector switch 30a, a pushbutton 30b, and an actuator arm 52. The dispenser 40 also includes circuitry, the microprocessor 22, the motor 26, the LED 32, and the sensor 28, which are provided within the housing 44 and shown generally in FIG. 1.

The microprocessor 22 controls the motor 26 during a spray operation to actuate the actuator arm 52, which depresses a valve stem 54 of the aerosol container 42 to dispense the contents therefrom. The microprocessor 22 includes programming to initiate a spray operation in response to a signal generated by the switch 30a, the pushbutton 30b, a timer, or the sensor 28. The timer can be implemented in the microprocessor 22 or as a separate component. For example, in one embodiment, the microprocessor 22 includes programming to control the dispenser 40 in a timed automatic actuation mode, wherein the dispenser 40 performs spray operations at specified time intervals, e.g., every 30 minutes. Alternatively, or in conjunction with the previous embodiment, the microprocessor 22 is programmed to perform a spray operation in response to a signal from the sensor 28, the selector switch 30a, and/or the pushbutton 30b.

For purposes of illustration only, one particular embodiment of the operation of the dispenser 40 will be described with particularity. Turning again to FIG. 2, in the present embodiment the selector switch 30a is used to turn the dispenser 40 on and off and to select between various operating modes, which may include a timed mode, a sensing mode, a combined timed and sensing mode, and other user selectable or pre-programmed functional modes and timing sequences. The LED 32 is energized continuously or is energized and de-energized to flash and indicate that the dispenser 40 is on and operating normally and/or to provide a warning that the dispenser 40 is about to perform a spray operation. The pushbutton 30b is provided for manual actuation of the aerosol container 42, wherein the pushbutton 30b may be depressed by a user to cause a spraying operation at any time, except when the dispenser 40 is off. The pushbutton 30b allows the user to manually override the automatic actuation of the device 40. The sensor 28 in the present embodiment is a photocell light sensor, which may be used to detect motion. However, any other type of motion detector may be utilized, e.g., a passive infrared or pyroelectric motion sensor, an infrared reflective motion sensor, an ultrasonic motion sensor, or a radar or microwave radio motion sensor. Further, the sensor 28 can be replaced or used in combination with any other type of known sensor, e.g., a heat sensor or an odor sensor.

Figure 3:
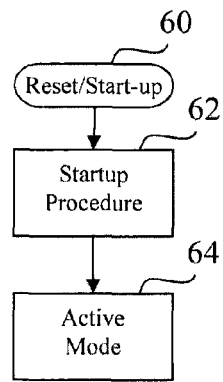
FIG. 3 is a flowchart that illustrates programming that may be executed by the dispensers of FIGS. 1 and/or 2.

Referring to FIG. 3, the programming implemented by the microprocessor 22 to control the dispenser 40 initiates at a reset/start-up block 60 when the selector switch 30a is toggled into an on position or, if the selector switch 30a is not provided, when new batteries 46 are inserted into the device 40. After the block 60, control passes to block 62 and a startup procedure is performed, following which control passes directly to a block 64 without any lockout period therebetween and an active mode procedure is performed, as will be described in greater detail hereinafter.

Figure 4:
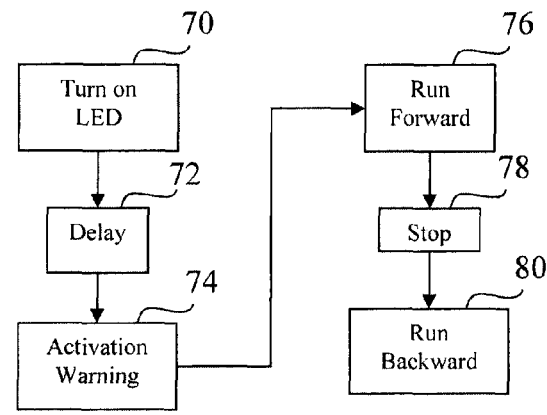
FIG. 4 is a flowchart that illustrates another embodiment of the programming of FIG. 3, including further details of a startup procedure.

FIG. 4 illustrates programming that provides further details according to one embodiment of the startup procedure 62, wherein control begins at a block 70 to provide an indication that the dispenser 40 is on, e.g., by energizing the LED 32. Next, control passes to a delay block 72 and control pauses for a predetermined period of time, e.g., about five seconds. Following the delay block 72, control passes to a block 74 and a warning or notice is issued that an activation sequence is imminent. In the present embodiment, the warning is a flashing or flickering of the LED 32, wherein the microprocessor 22 energizes and de-energizes the LED 32 two or more times within a short period of time, e.g., within three seconds. However, in other embodiments, the warning can be any combination of a visual, audible, tactile, olfactory, or any other warning that would be apparent to one of ordinary skill in the art. Following the block 74, the programming performs an activation sequence. In the present embodiment, the activation sequence is a spray operation that includes blocks 76, 78, and 80. More specifically, the spray operation begins at the block 76 where the motor 26 is energized to move the actuator arm 52 downwardly to depress the valve stem 54 of the aerosol container 42 into an open position. The motor 26 is deenergized in block 78. Thereafter, the motor 26 is energized to move the actuator arm 52 in the opposite direction in block 80 to assist the valve stem 54 in moving to a closed and non-depressed position. In one embodiment, the motor 26 is energized during the block 76 for about 1 second, the motor 26 is deenergized during the block 78 for about 150 milliseconds, and the motor 26 is energized during the block 80 for about 400 milliseconds. Modifications to the activation sequence of the present embodiment can include any sequence of the same or different steps, as would be apparent to one of ordinary skill in the art.

Referring again to the delay block 72, a relatively short delay of about five seconds or less is provided before the activation warning and the activation sequence are performed. In this embodiment, the short delay allows a user to quickly determine that the dispenser 40 is functioning properly, e.g., that all of the components are properly coupled together and functioning and that the contents of the container 42 are not depleted. Consequently, an improved user interaction with the dispenser 40 can be provided over other dispensers that require a user to wait for a longer period before being able to confirm the proper functioning of the dispenser.

Figure 5:
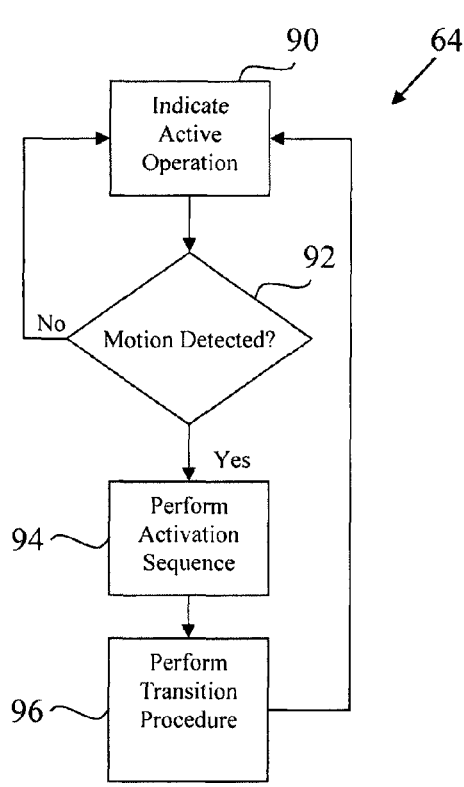
FIG. 5 is a flowchart that illustrates programming that may be executed during an active mode procedure of the dispensers of FIGS. 1 and/or 2.

FIG. 5 illustrates an embodiment of programming executed during the active mode procedure 64. At a block 90 the dispenser 40 turns on the LED 32 to provide an indication that the dispenser 40 is in the active mode. Thereafter, control passes to a decision block 92 and the programming activates the sensor 28 to determine if motion is detected. If motion is not detected, control passes back to the block 90 and subsequently proceeds again to the block 92. However, if motion is detected, control passes to a block 94 to perform an activation sequence, which may be the same or different from the activation sequence described above in relation to FIG. 4. After the activation sequence is performed, control passes to a block 96 to perform a user selectable or pre-programmed transition procedure before control loops back to the block 90.

Figure 6:
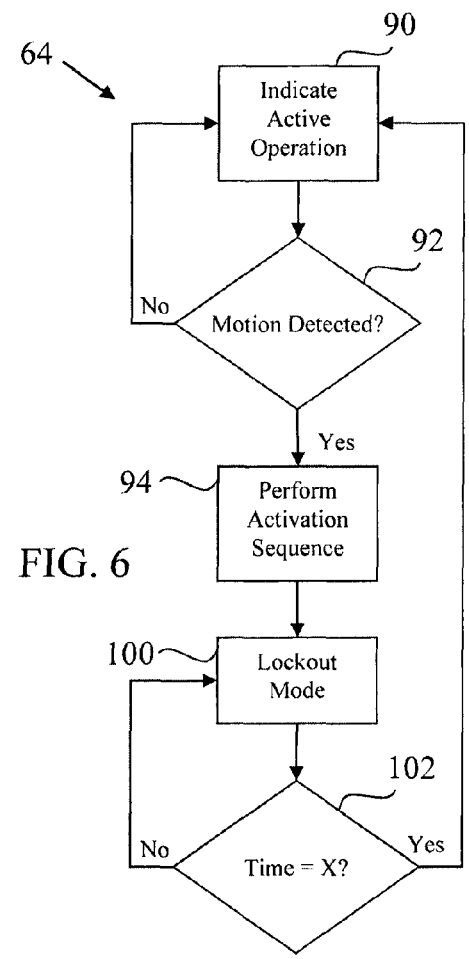
FIG. 6 is a flowchart that illustrates another embodiment of the active mode procedure of FIG. 5.

FIGS. 6-8 provide details of various non-limiting embodiments of the transition procedure of the block 96 of FIG. 5. In FIG. 6, the transition procedure includes blocks 100 and 102, which provides for a lockout mode, wherein the sensor 28 is deactivated, e.g., by ignoring the output from the sensor and/or de-energizing the sensor, and the dispenser does not perform an activation sequence in response to the detection of motion. However, an activation sequence may still be performed if the pushbutton 30b is depressed. The decision block 102 determines if the time elapsed during the lockout mode has reached a certain lockout period X. If the lockout period X has elapsed, then control passes back to the blocks 90-94 to determine if an activation sequence should be performed in response to motion. If the lockout period X has not elapsed, then control loops back to the lockout mode of the block 100. In one embodiment, a user can use an input device such as the switch 30a to select the length of the lockout period X. For example, the user can select different lockout periods ranging from 5 min, 20 min, 30 min, 60 min, etc. for different sized rooms or user preferences. In a different embodiment, the lockout period may be a pre-programmed period.

In FIG. 7, the transition procedure includes blocks 110-116. More specifically, at a block 110 the control implements a lockout mode as described above. However, in the present embodiment, the control performs one or more automatic activation sequences during the lockout period. For example, the decision block 112 determines if the elapsed time during the lockout mode is equal to a time X and, if so, control passes to a block 114 to perform an activation sequence. After the block 114, control passes back to the block 110 and subsequently to the block 112. If the block 112 determines that the elapsed time is not equal to X, control passes to the block 116, which determines if the elapsed time is equal to Y, which in the present embodiment represents the total lockout period. If the elapsed time has not reached the total lockout period Y, then control passes back to the block 110, while if the lockout period Y has elapsed then control passes back to the block 90. In one embodiment, the user can use an input device such as the switch 30a to select the length of the total lockout period, the number of automatic activation sequences during the lockout period, and the times at which the automatic activation sequence(s) are performed. In one example, the user selects a 30 min lockout period and a single automatic activation sequence at 15 min into the lockout period. In another example, the user selects a 60 min lockout period and a first automatic activation sequence at 20 min and a second automatic activation sequence at 40 min into the lockout period. In yet a further example, the user selects a 40 min lockout period and a single activation sequence at 10 min into the lockout period. In a different embodiment, one or more of the total lockout periods, the number of automatic activation sequences, and the times at which the automatic activation sequences are performed may be pre-programmed.

In FIG. 8, the transition procedure includes blocks 130-138. More specifically, at the block 92 if motion is not detected, then control passes back to the block 90, as discussed above. However, if motion is detected at the block 92, then control passes to a block 130, which determines how many times that motion has been detected and an activation or spray sequence performed. If motion has been detected and an activation sequence performed X times, then control passes to the block 132 and another activation sequence is performed before control passes to a lockout mode of the block 136 and the decision block 138. The decision block 138 determines if the lockout period has expired, as described above. Referring back to the block 130, if motion has not been detected and an activation sequence performed X times, then control passes to the block 132 and an activation sequence is performed before control passes back to the block 90. In the present embodiment, control does not execute a lockout mode until a second or subsequent motion detection/activation sequence is performed. The user can use an input device such as the switch 30a to select the number of motion detection/activation sequences that are to be performed before entering the lockout mode. For example, the user can set the switch 30a so that control executes the lockout mode only after a second, third, fourth, etc. motion detection/activation sequence is performed. In other embodiments, the number of motion detection/activation sequences that are to be performed before entering the lockout mode is preprogrammed.

In the embodiments described in relation to FIGS. 3-8, the programming performs the active mode after the startup procedure without any lockout period therebetween, which allows the user to execute the sensor based operation of the active mode without waiting for a lockout period to expire. Consequently, a user can confirm the proper operation of the sensor quickly upon startup of the dispenser. For example, after the startup procedure is performed, the user can immediately test the sensor by waving their hand in front of the sensor to trigger an activation sequence. Further, the user can immediately test the sensitivity of the sensor by waving their hand at different distances from the sensor and/or at different speeds/amplitudes. As a result, the user can quickly and conveniently determine a preferred placement of the dispenser in a room.

Various modifications can be made to the above embodiments without departing from the spirit of the present disclosure. For example, the user can use the switch 30a to adjust the number of activation sequences that are performed each time motion is sensed, e.g., between one, two, or three activations each time motion is detected. According to another example, the user can use the switch 30a to adjust a lockout period between the startup procedure and the active mode between zero and twenty minutes, for example. Further, other embodiments of the disclosure including all the possible different and various combinations of the individual features of each of the foregoing described embodiments are specifically included herein.

INDUSTRIAL APPLICABILITY

The dispenser described herein advantageously allows for the contents of a container to be sprayed into the atmosphere in a manner that can be adjusted by a user to accommodate different room conditions, environmental conditions, and personal preferences.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

I claim:

1. A method of operating a dispensing unit, comprising the steps of:
    applying a power source to a dispensing unit that includes a container;
    performing a startup procedure in response to applying the power source, wherein the startup procedure includes performing an activation sequence that discharges a fluid from the container; and
    performing an active mode procedure after the startup procedure without providing a lockout period therebetween, wherein the active mode procedure includes activating a sensor associated with the dispensing unit, performing an activation sequence that discharges the fluid from the container when the sensor detects sensory input, and performing a transition procedure.

2. The method of claim 1, wherein the step of performing the transition procedure includes providing a lockout period during which the sensor is deactivated and performing a subsequent active mode procedure after the expiration of the lockout period, and wherein the length of the lockout period is selectable by a user.

3. The method of claim 1, wherein the step of performing the transition procedure includes providing a timeout period during which the sensor is deactivated, performing one or more automatic activation sequences during the timeout period, and performing a subsequent active mode procedure after the expiration of the timeout period.

4. The method of claim 3, wherein a user can select one or more of the length of the timeout period, the number of automatic activation sequences during the timeout period, and the timing of the one or more automatic activation sequences during the timeout period.

5. The method of claim 1, wherein the step of performing the transition procedure includes performing subsequent activation sequences in response to the sensor detecting subsequent sensory input and providing a timeout period during which the sensor is deactivated only after performing one or more subsequent activation sequences.

6. The method of claim 5, wherein a user can select the number of subsequent activation sequences to be performed before providing the timeout period.

7. The method of claim 1, wherein the step of performing the transition procedure includes performing one or more activation sequences each time sensory input is sensed.

8. The method of claim 7, wherein a user can select the number of activation sequences performed each time sensory input is sensed.

9. The method of claim 1, wherein the step of performing the startup procedure further includes the steps of providing an indication that the dispensing unit is functioning properly, providing a sleep period that lasts about five seconds, providing an indication that the activation sequence is about to be performed, and performing the activation sequence.

10. A method of operating a dispensing unit, comprising the steps of:
    applying a power source to a dispensing unit that includes a container;
    performing a startup procedure in response to applying the power source, wherein the startup procedure includes performing an activation sequence that discharges a fluid from the container; and
    performing an active mode procedure after the startup procedure without providing a lockout period therebetween, wherein the active mode procedure includes detecting sensory input by a sensor associated with the dispensing unit and performing a transition procedure.

11. The method of claim 10, further comprising the step of performing an activation sequence during the active mode procedure upon detecting sensory input by the sensor.

12. The method of claim 10, further comprising the step of performing an activation sequence during the transition procedure upon detecting sensory input by the sensor during the active mode procedure.

13. The method of claim 10, wherein the transition procedure includes at least one lockout period and at least one activation sequence.

14. The method of claim 13, wherein at least one of the lockout period and the activation sequence of the transition procedure is user-selectable.

15. The method of claim 11, wherein the activation sequence performed in the active mode procedure is a different activation sequence than performed in the startup procedure.

16. The method of claim 10, wherein the activation sequence performed in the start-up procedure is performed in at least one of the active mode procedure and the transition procedure.

17. A method of operating a dispensing unit, comprising the steps of:
    applying a power source to a dispensing unit that includes a container;
    performing a startup procedure in response to applying the power source, wherein the startup procedure includes providing a sleep period and performing an activation sequence that discharges a fluid from the container immediately after the sleep period has elapsed; and
    performing an active mode procedure after the startup procedure, wherein the active mode procedure includes activating a sensor associated with the dispensing unit, performing an activation sequence that discharges the fluid from the container when the sensor detects sensory input, and performing a transition procedure,
    wherein the transition procedure includes providing a timeout period during which one or more automatic activation sequences are performed independent of any sensory input and a subsequent active mode procedure is initiated after the expiration of the timeout period.

18. The method of claim 17, wherein the sensor is deactivated during the timeout period.

19. The method of claim 17, wherein any sensory input detected by the sensor is not registered to cause the dispensing unit to perform the one or more automatic activation sequences during the timeout period.

20. The method of claim 17, wherein the active mode procedure is performed after the startup procedure without a timeout period therebetween, and wherein the user can select one or more of the length of the timeout period, the number of automatic activation sequences during the timeout period, and the timing of the one or more automatic activation sequences during the timeout period.

* * * * *